United States Patent
Welz et al.

(10) Patent No.: US 10,132,782 B2
(45) Date of Patent: Nov. 20, 2018

(54) APPARATUS FOR FIELD-FLOW FRACTIONATION

(71) Applicant: Postnova Analytics GmbH, Landsberg (DE)

(72) Inventors: Roland Welz, Schongau (DE); Thorsten Klein, Schondorf (DE)

(73) Assignee: Postnova Analytics GmbH, Landsberg (DE)

( * ) Notice: Subject to any disclaimer, the term of this patent is extended or adjusted under 35 U.S.C. 154(b) by 0 days.

(21) Appl. No.: 15/042,398

(22) Filed: Feb. 12, 2016

(65) Prior Publication Data

US 2016/0238571 A1    Aug. 18, 2016

(30) Foreign Application Priority Data

Feb. 13, 2015   (DE) ........................ 10 2015 202 667

(51) Int. Cl.
    *G01N 30/00*    (2006.01)
    *B01D 11/04*    (2006.01)
    *G01N 30/74*    (2006.01)

(52) U.S. Cl.
    CPC ......... *G01N 30/0005* (2013.01); *B01D 11/04* (2013.01); *G01N 30/74* (2013.01); *G01N 2030/003* (2013.01)

(58) Field of Classification Search
    CPC ......... G01N 30/0005; G01N 2030/003; G01N 30/74; G01N 30/32; B01D 11/04
    See application file for complete search history.

(56) References Cited

U.S. PATENT DOCUMENTS

| | | | | |
|---|---|---|---|---|
| 4,214,981 A | * | 7/1980 | Giddings | B03B 5/00 209/1 |
| 5,039,426 A | * | 8/1991 | Giddings | B01D 21/00 209/127.1 |
| 5,141,651 A | * | 8/1992 | Giddings | B01L 3/502753 209/131 |
| 5,163,979 A | * | 11/1992 | Patrick | G01N 30/32 73/23.36 |
| 5,193,688 A | * | 3/1993 | Giddings | B03B 5/00 209/127.1 |

(Continued)

OTHER PUBLICATIONS

Messaud et al., An overview on field-flow fractionation techniques and their applications in the separation and characterization of polymers, Progress in Polymer Science 2009. Jan. 1, 2009.

(Continued)

*Primary Examiner* — Mohamed K Amara
(74) *Attorney, Agent, or Firm* — Hodgson Russ LLP

(57) ABSTRACT

The present invention relates to an apparatus for field-flow fractionation and to a method for separating samples by means of field-flow fractionation using this apparatus. The apparatuses of the invention comprise a separation channel which, in addition to a first outlet for sample-containing solvent, comprises a second outlet for sample-free solvent, wherein the second outlet is arranged in a region of the separation channel from which sample-free solvent may be removed during elution and a flow volume control device is arranged downstream of the second outlet. They are characterized in that the flow volume control device is a mass flow controller.

12 Claims, 6 Drawing Sheets

(56) References Cited

U.S. PATENT DOCUMENTS

| | | | | |
|---|---|---|---|---|
| 5,531,959 | A * | 7/1996 | Johnson | G01N 30/00 210/198.2 |
| 5,606,111 | A * | 2/1997 | Pili e | G01N 1/22 73/19.12 |
| 5,932,100 | A * | 8/1999 | Yager | B01D 11/0492 210/511 |
| 5,948,684 | A * | 9/1999 | Weigl | B01F 5/0403 422/81 |
| 6,109,119 | A * | 8/2000 | Jiang | B03B 5/00 209/156 |
| 6,130,358 | A * | 10/2000 | Tolleson | B01J 31/185 568/451 |
| 6,221,677 | B1 * | 4/2001 | Wu | G01N 33/5005 210/198.2 |
| 6,365,050 | B1 * | 4/2002 | Cauchon | G01N 30/0005 209/131 |
| 6,541,213 | B1 * | 4/2003 | Weigl | B01F 5/0403 210/198.2 |
| 6,641,708 | B1 * | 11/2003 | Becker | B03C 5/026 204/547 |
| 6,790,330 | B2 * | 9/2004 | Gascoyne | B03C 5/026 204/547 |
| 8,431,340 | B2 * | 4/2013 | Jovanovich | B01F 11/0071 204/451 |
| 8,535,536 | B1 * | 9/2013 | Gale | B01D 57/00 210/198.1 |
| 8,883,512 | B1 * | 11/2014 | Mawson | G01N 33/6893 436/127 |
| 8,931,644 | B2 * | 1/2015 | Lean | B03B 5/32 209/362 |
| 9,220,831 | B2 * | 12/2015 | Ingber | A61M 1/36 |
| 9,399,797 | B2 * | 7/2016 | Hutchison | C12Q 1/686 |
| 2001/0001575 | A1 * | 5/2001 | Anderson, Jr. | G01N 27/44721 356/337 |
| 2003/0019812 | A1 * | 1/2003 | Berger | B01D 11/0203 210/656 |
| 2004/0000519 | A1 | 1/2004 | Jiang et al. | |
| 2008/0128331 | A1 * | 6/2008 | Lean | B03B 5/32 209/155 |
| 2008/0164194 | A1 * | 7/2008 | Hedberg | B01D 1/14 210/198.2 |
| 2010/0040483 | A1 * | 2/2010 | Berger | F04B 11/0075 417/205 |
| 2013/0015138 | A1 * | 1/2013 | Schlake | B01D 15/165 210/656 |
| 2015/0338382 | A1 * | 11/2015 | Guan | G01N 30/28 73/23.42 |
| 2016/0011155 | A1 * | 1/2016 | Klein | G01N 30/0005 73/61.56 |
| 2018/0065078 | A1 * | 3/2018 | Hayes | C01B 23/0057 |

OTHER PUBLICATIONS

Jonsson et al., Flow Field Flow Fractionation in Hollow Cylindrical Fibers, Anal. Chem. 1989, 61, 11-18. Jan. 1, 1988.

Prestel et al., Increasing the Sensitivtity of Asymmetrical Flow Field-Flow Fractionation: Slot Outlet Technique, Anal. Chem, Vo. 78, No. 18, pp. 6664-6669. Sep. 15, 2006.

* cited by examiner

APPARATUS FOR FIELD-FLOW FRACTIONATION

TECHNICAL FIELD

The present invention relates to an apparatus for field-flow fractionation and to a method for separating samples by means of field-flow fractionation using this apparatus.

PRIOR ART

Field-flow fractionation (FFF) is a quasi-chromatographic method of analysis for separating macromolecular and colloidal samples. In contrast to chromatography, sample separation in field-flow fractionation does not take place in a packed column, but in an open separation channel which does not contain a stationary phase.

Owing to the low height of the separation channel, a laminar flow with a parabolic flow profile is formed within the separation channel. Separation of the samples is carried out by a force or separation field which is applied vertically to this flow within the separation channel. Under the influence of the applied separation field and the counter-acting diffusion of the sample particles, the individual components of the sample are separated. First, a state of equilibrium will occur in which the sample is forced towards a wall of the separation channel (the so-called accumulation wall) under the influence of the separation field, the individual sample components being present in the separation channel in separate layers with a specific layer thickness. Smaller particles with a larger diffusion coefficient reach layers in a higher position, i.e. at a greater distance from the accumulation wall, and thus regions of higher flow rates. These elute first. Larger particles with a lower diffusion coefficient move in layers that are therefore further down, i.e. closer to the accumulation wall, and are thus in regions with a lower flow rate with the result that they elute later.

Depending on the manner in which the separation field used is generated, i.e. the physical nature of this field, different field-flow fractionation techniques have been developed. These comprise flow field-flow fractionation, sedimentation field-flow fractionation, such as e.g. centrifugal field-flow fractionation, and thermal field-flow fractionation. Among these, flow field-flow fractionation with the sub-techniques of symmetrical flow field-flow fractionation, asymmetrical flow field-flow fractionation (AF4) and hollow-fiber flow field-flow fractionation (HF5) is the most common.

An overview of various field-flow fractionation techniques and the corresponding theoretical background can be found, for example, in F. A. Messaud et al., "An overview on field-flow fractionation techniques and their applications in the separation and characterization of polymers", Progress in Polymer Science, 34(4), pages 351-368. Hollow-fiber flow field-flow fractionation is described, for example, in Jonsson and Carlshaf, "Flow field flow fractionation in hollow cylindrical fibers" Anal. Chem. 61(1), pages 11-18.

For analysis of a sample by means of field-flow fractionation, the sample is first of all injected into the separation channel. Depending upon the sub-technique used, focusing or equilibration of the sample then takes place in the separation channel. After focusing or equilibration is completed, the sample is then eluted from the separation channel and can be detected.

During elution, sample-free solvent can be removed from the separation channel. This leads to concentration of the sample in the remaining solvent, which is led through the detector(s). This increases measuring sensitivity and at the same time lowers the detection limit. Removing of sample-free solvent is facilitated by the fact that, due to the movement of the sample towards the accumulation wall under the influence of the separation field during elution, regions are created inside the separation channel, in which the solvent does not contain any sample, i.e. regions with sample-free solvent. These occur in particular in the region of the wall of the separation channel opposite the accumulation wall. In hollow-fiber flow field-flow fractionation, regions with sample-free solvent occur in the center of the hollow-fiber separation channel. Sample-free solvent can be removed through a separate outlet of the respective separation channel. For this, the corresponding outlet must be arranged in a region of the separation channel with sample-free solvent.

The basic principle of concentrating a sample in the separation channel of a field-flow fractionation system by removing sample-free solvent is described in US 2004/0000519 or in U.S. Pat. No. 5,193,688, for example. The technique is known as Smart Stream, Smart Stream Splitting, Slot Outlet and also Frit Outlet. A possibility for a technical implementation is described in Prestel et al., "Increasing the Sensitivity of Asymmetrical Flow Field-Flow Fractionation: Slot Outlet Technique", Analytical Chemistry 2006, 78, pages 6664-6669. The separation channel of the apparatus for asymmetrical flow field-flow fractionation (AF4) used therein has a further outlet for sample-free solvent (Slot Outlet; SO) in addition to the outlet for sample-containing solvent. In the apparatus described by Prestel et al., the flow of the sample-free solvent (SO flow) out of the corresponding outlet is controlled by means of a syringe pump with two pistons operating in opposite directions, i.e. in pendulum mode.

However, using syringe pumps to regulate the slot outlet flow also has disadvantages. It only provides regulation rather than control, which means that the actual flow rates are not monitored and can therefore vary slightly. Moreover, two syringe pump units operating in pendulum mode are required for a constant flow volume over a longer period, which increases the size of the assembly and results in higher costs. Besides, pulsations can be generated in pendulum mode by switching between the individual syringes. In the application for regulating the Slot Outlet flow described here, these pulsations impair the laminar flow profile inside the separation channel. Disruption of the laminar flow adversely affects the signal-to-noise ratio and so impairs the detector signal and hence measuring accuracy. Moreover, as a rule, the syringes used have poor pressure stability and therefore limit the development of systems for high-pressure applications operating at pressures of up to 150 bar. Finally, syringe pump systems must be installed in an upright position, which is necessary to allow the syringes to be vented on start-up. Poor venting again leads to pulsations which, as already described, impair the laminar flow profile inside the separation channel. Hence the upright mounting position also limits the potential for developing more compact devices.

The object of the present invention is therefore to provide an improved apparatus for field-flow fractionation which is characterized by a simplified design and a better signal-to-noise ratio of the detector signal(s).

DESCRIPTION OF THE INVENTION

This object is achieved by the apparatuses of the present invention. The apparatuses of the present invention are apparatuses for field flow fractionation and comprise a separation channel, that, in addition to a first outlet for sample-containing solvent, has a second outlet for sample-free solvent, wherein the second outlet is arranged in a region of the separation channel from which sample-free solvent can be removed during elution, and a flow volume control device is arranged downstream of the second outlet. The apparatuses of the invention are characterized in that the flow volume control device is a mass flow controller.

The apparatuses of the invention are apparatuses for field-flow fractionation. Accordingly, the apparatuses of the invention comprise one or more pump(s), a sample injection system, a separation channel and one or more detector(s). The apparatuses of the invention may further comprise one or more reservoir(s) and one or more waste container(s).

The apparatuses of the invention may comprise reservoirs for one or more carrier liquid(s), i.e. for one or more solvents. Measurements in the apparatuses of the invention are preferably carried out with one solvent so that the apparatuses of the invention preferably comprise one reservoir. Alternatively, operation with more than one solvent is possible so that solvent can automatically be mixed in a constant ratio for a measurement but gradient elution can also be carried out. The apparatuses of the invention may therefore also comprise two or more reservoirs.

Aqueous and non-aqueous organic solvents may be used as solvents in the apparatuses of the invention. Examples include aqueous solvents with 0.5-5 g/l NaCl and/or 0.1-5 g/l sodium dodecyl sulfate (SDS) and the organic solvents tetrahydrofurane (THF), toluene, acetone, methanol, ethanol, chloroform, dimethyl formamide (DMF) and dimethyl sulfoxide (DMSO) and mixtures thereof.

Any pump suitable for use in field-flow fractionation or liquid chromatography (LC) may be used as the pump in the apparatuses of the invention, such as an HPLC pump, for example. Preferably an HPLC pump is used, wherein this may be designed as an isocratic, binary, ternary or quaternary pump. The pump is provided for conveying the solvent at a defined constant flow rate.

The apparatuses of the invention comprise either one pump or two pumps for conveying the solvent. The apparatuses of the invention preferably comprise only one pump for conveying the solvent. Apparatuses for field-flow fractionation with only one pump are described in DE 20 2014 101 518 U1, for example.

A sample injection system for use in the apparatuses of the invention may be an injection valve to be operated manually or an autosampler connected upstream, i.e. installed upstream, of the separation channel.

The sample injection system is preferably an autosampler.

The separation channel of the apparatuses of the invention may be a separation channel for flow field-flow fractionation such as e.g. symmetrical flow field-flow fractionation, asymmetrical flow field-flow fractionation (AF4) or hollow-fiber flow field-flow fractionation. The separation channel may additionally be a separation channel for sedimentation field-flow fractionation such as e.g. centrifugal field-flow fractionation, or a separation channel for thermal field-flow fractionation.

The separation channel of the apparatuses of the invention is preferably a separation channel for symmetrical flow field-flow fractionation, asymmetrical flow field-flow fractionation (AF4), centrifugal field-flow fractionation or thermal field-flow fractionation.

A separation channel for field-flow fractionation comprises at least one inlet at a first end and a first outlet at a second end. During elution, sample-containing solvent is led through the outlet of the separation channel towards the detector(s). In addition to the first outlet for sample-containing solvent, the separation channel of the apparatuses of the invention comprises a second outlet for sample-free solvent. The second outlet is arranged in a region of the separation channel from which sample-free solvent can be removed during elution. The second outlet is preferably arranged upstream of the first outlet for sample-containing solvent. The second outlet is particularly preferably arranged in the wall opposite the accumulation wall of the separation channel.

Removing sample-free solvent from the separation channel during elution leads to concentration of the sample in the remaining solvent, which is led through the first outlet for sample-containing solvent and through the detector(s). This increases measuring sensitivity and at the same time lowers the detection limit.

Sample-free solvent within the meaning of the present invention means that the solvent does not contain any sample particles. Regions in which the solvent does not contain any sample particles arise in the separation channel during elution under the influence of the respective separation field that is applied. This results in a movement of the sample towards the accumulation wall of the separation channel and to enrichment of the sample in the region of the accumulation wall. As a result of this, the remaining regions of the separation channel, in particular the regions of the separation channel opposite the accumulation wall, do not contain any sample, i.e. are sample-free. In hollow-fiber flow field-flow fractionation, regions with sample-free solvent occur in the center of the hollow-fiber separation channel. The sample-free solvent can be removed through the second outlet of the separation channel of the apparatuses of the invention. The absence of sample in the removed solvent can be confirmed using suitable analytical techniques, such as HPLC, for example. The fact that the removed solvent is sample-free guarantees the desired concentration of the sample prior to detection. If the removed solvent were to contain (uncontrolled) quantities of sample, the effect of concentration and increasing measuring sensitivity would not be possible.

Removing the sample-free solvent is controlled by means of a flow volume control device. This is arranged downstream of the second outlet. This means that the flow volume control device may be directly connected with the second outlet of the separation channel and also via a shut-off or switching valve situated between the second outlet and the flow volume control device. The respective liquid connections between the separation channel and the flow volume control device or between the separation channel, the shut-off or switching valve and the flow volume control device are provided by means of suitable capillaries. However, the flow volume control device or the shut-off or switching valves may also be connected directly with the second outlet of the separation channel without a capillary. In this case the second outlet is designed as a valve seat. According to the invention, the flow volume control device is a mass flow controller.

By means of the mass flow controller the flow rate of the sample-free solvent removed during elution can be measured and set to a prescribed value and/or kept constant.

In connection with the present invention, the term "flow rate" means the volume of a solvent flowing through the apparatuses of the invention or parts thereof, such as the separation channel, the flow volume control device and the detector(s), per unit of time. The term "volume flow" will also be used instead of the term "flow rate".

Compared with the syringe pumps known from the prior art, the use of a mass flow controller to control the flow rate of the sample-free solvent removed during elution, i.e. to control the Slot Outlet flow, has several advantages: it produces a more compact assembly and does not limit the mounting position, pressure stability can be guaranteed up to 150 bar and controlling is possible depending on the actual flow rate measured. Because of the resulting uniform flow rate control of the sample-free solvent removed during elution with no pressure variations caused by the apparatus, one obtains a detector signal with a better signal-to-noise ratio.

Mass flow controllers are substantially made up of three components, a measuring unit, a regulating unit, e.g. a regulating valve, and the corresponding electronics (control line). Using different physical principles (Coriolis force, thermal transport, pressure differential, etc.) the measuring unit can determine the volume throughput in a flow path and transmit this reading to the electronics. Depending upon the physical measuring principle, this reading is set against corresponding material constants in order to determine a volume flow per unit of time. Depending upon the physical measuring principle, additional parameters such as density or temperature are determined in the measuring unit and transmitted to the electronics. This means that, depending upon the physical measuring principle, devices can also operate independently of preset material constants. The electronics have an interface so that a desired volume flow can be transmitted to the electronics. The electronics then perform a target/actual value comparison of the data obtained with the measuring unit and control the regulating unit accordingly, in order to set the desired volume flow. As a rule the regulating unit consists of a magnetically impelled stamp and a nozzle/bore. If the measured value/actual value exceeds the target value, the stamp is moved by means of the electronics further towards the bore and hence reduces the opening width of the flow path in which the mass flow controller is integrated. This increases the flow resistance of the mass flow controller and the flow rate through the control unit decreases. Since target value and actual value are constantly monitored by the electronics, the stamp can be set up so that there is a constant flow rate with the desired force through the mass flow controller.

A mass flow controller suitable for use in the apparatuses of the invention comprises a measuring unit and a regulating valve, which are connected to each other via a control line. As previously described, the regulating valve is opened and closed via the control line depending on a target/actual value comparison of the data obtained with the measuring unit.

The regulating valve may be installed upstream or downstream of the measuring unit. The regulating valve is preferably installed downstream of the measuring unit.

The separation channel of the apparatuses of the invention may comprise a second inlet for sample injection that is arranged at the first end of the separation channel downstream of the first inlet.

If the separation channel of the apparatuses of the invention is a separation channel for flow field-flow fractionation, then the separation channel additionally comprises a connection for the cross-flow, i.e. a connection via which the liquid flow of the cross-flow can be removed from the separation channel. This is arranged below the accumulation wall of the separation channel. Although the region below the accumulation wall likewise contains no sample particles, it is situated outside the separation channel and is therefore not a region of the separation channel within the meaning of the present invention and the above explanations, from which sample-free solvent can be removed during elution.

Conventional AF4 separation channel modules comprising a carrier, a frit, a semi-permeable membrane, a spacer and a cover may be used as AF4 separation channel to be employed in the apparatuses of the invention. In another embodiment, the frit and the semi-permeable membrane may also be formed in one piece. Corresponding separation channel modules are described in EP 1 879 025 A1, for example.

The semi-permeable membranes for use in an AF4 separation channel of the apparatuses of the invention are size exclusion membranes. The cut-off of the semi-permeable membranes is at 5 Da to 100 kDa, preferably at 100 Da to 30 kDa, and especially preferably at 10 kDa. It is preferred to use regenerated cellulose (RC), polyether sulfone (PES) or polyvinylidene fluoride (PVDF) as the material for the semi-permeable membranes.

In addition to the inlet, the first outlet, the connection for the cross-flow and the second outlet for sample-free solvent, an AF4 separation channel for use in the apparatuses of the invention may also have an additional connection for the focus flow, which is arranged between the inlet and the second outlet for sample-free solvent. Solvent is pumped into the separation channel during focusing of the sample through this additional connection.

Detector(s) that may be used in the apparatuses of the invention may be any detectors that are known in the field of field-flow fractionation or high-performance liquid chromatography (HPLC). Examples are UV detectors, refractive index (RI) detectors, (multi-angle) light scattering detectors, mass spectrometers, fluorescence detectors, ICP mass spectrometers, dynamic light scattering detectors (DLS), and small-angle X-ray scattering (SAXS) detectors.

Preferably the detector(s) is/are a UV detector, a refractive index (RI) detector and/or a (multi-angle) light scattering detector.

The apparatuses of the invention preferably comprise one or two pump(s), an autosampler as sample injection system, a separation channel, a UV detector, a refractive index (RI) detector and/or a (multi-angle) light scattering detector as detector(s), wherein the separation channel comprises, in addition to the first outlet for sample-containing solvent, a second outlet for sample-free solvent, the second outlet is arranged in a region of the separation channel from which sample-free solvent can be removed during elution, and a mass flow controller as flow volume control device is arranged downstream of the second outlet.

Particularly preferably the apparatuses of the invention are apparatuses for flow field-flow fractionation, comprising a pump, a first flow volume splitting device, a first mass flow controller arranged downstream of the flow volume splitting device, a sample injection system, a separation channel with an inlet at a first end, a first outlet for sample-containing solvent at a second end, a connection for the cross-flow and a second outlet for sample-free solvent, which is arranged between the inlet and the first outlet, a second mass flow controller arranged downstream of the second outlet, a second flow volume splitting device, a first back-pressure element, a second back-pressure element, one or more detector(s) and a cross-flow control device, wherein the solvent stream generated by the pump is divided by means of the first flow volume splitting device into a first flow path and a second flow path, the first flow path leads via the first mass flow controller and the sample injection system to the inlet at the first end of the separation channel, the second flow path leads via the second back-pressure element to the second flow volume splitting device, which divides the solvent stream between the first outlet for sample-containing solvent at the second end of the separation channel and a third flow path, which leads via the first back-pressure element to the detector(s), and the cross-flow control device is connected with the separation channel via a fourth flow path and the connection for the cross-flow.

Alternatively, particularly preferred apparatuses of the invention for flow field-flow fractionation comprise a pump, a first flow volume splitting device, a first mass flow controller arranged downstream of the flow volume splitting device, a sample injection system, a separation channel with an inlet at a first end, a first outlet for sample-containing solvent at a second end, a connection for the cross-flow and a second outlet for sample-free solvent that is arranged upstream of the first outlet, and an additional connection for the focus flow that is arranged between the inlet and the second outlet, a second mass flow controller arranged downstream of the second outlet, a first back-pressure element, a second back-pressure element, one or more detector(s) and a cross-flow control device, wherein the solvent stream generated by the pump is divided by means of the first flow volume splitting device into a first flow path and a second flow path, the first flow path leads via the first mass flow controller and the sample injection system to the inlet at the first end of the separation channel, the second flow path leads via the second back-pressure element to the additional connection for the focus flow of the separation channel, a third flow path leads from the first outlet for sample-containing solvent at the second end of the separation channel via the first back-pressure element to the detector(s) and the cross-flow control device is connected with the separation channel via a fourth flow path and the connection for the cross-flow.

The cross-flow control device of the particularly preferred apparatuses of the invention for flow field-flow fractionation can either be a syringe pump system or a mass flow controller.

The separation channel of the particularly preferred apparatuses of the invention for flow field-flow fractionation is preferably an AF4 separation channel, in which the second outlet for sample-free solvent is arranged opposite the accumulation wall of the separation channel.

A UV detector, a refractive index (RI) detector and/or a (multi-angle) light scattering detector is/are preferably used as detector(s) in the particularly preferred apparatuses of the invention for flow field-flow fractionation.

Further preferably, the apparatuses of the invention are apparatuses for thermal or centrifugal field-flow fractionation, comprising a pump, a flow volume splitting device, a sample injection system arranged downstream of the flow volume splitting device, a separation channel with an inlet at a first end, a first outlet for sample-containing solvent at a second end, a second outlet for sample-free solvent that is arranged between the inlet and the first outlet, a mass flow controller arranged downstream of the second outlet and one or more detector(s), wherein the solvent stream generated by the pump is divided by means of the flow volume splitting device into a first flow path, a second flow path and a third flow path, the first flow path leads via the sample injection system to the inlet at the first end of the separation channel, the second flow path connects the flow volume splitting device with the detector(s) and the third flow path connects the flow volume splitting device with the first outlet of the separation channel.

A UV detector, a refractive index (RI) detector and/or a (multi-angle) light scattering detector is/are preferably used as detector(s) in the apparatuses for thermal or centrifugal field-flow fractionation.

In a further embodiment the present invention relates to the use of the apparatuses of the invention in a method for analyzing a sample by means of field-flow fractionation. The method comprises the following steps:
(i) injection of a sample into the separation channel using a solvent, and
(ii) elution of the sample with the solvent from the separation channel under the influence of a separation field and detection of the fractionated sample with one or more detector(s), wherein sample-free solvent is simultaneously removed from the separation channel via the second outlet of the separation channel and the second mass flow controller arranged downstream of said outlet.

In a further embodiment the present invention relates to the use of the apparatuses of the invention in a method for analyzing a sample by means of flow field-flow fractionation. The method comprises the following steps:
(i) injection of a sample into the separation channel using a solvent,
(ii) focusing the sample with the aid of the solvent in the separation channel, and
(ii) elution of the sample with the solvent from the separation channel under the influence of a separation field and detection of the fractionated sample with one or more detector(s), wherein sample-free solvent is simultaneously removed from the separation channel via the second outlet of the separation channel and the second mass flow controller arranged downstream of said outlet.

In a further embodiment the present invention relates to the use of the apparatuses of the invention in a method for analyzing a sample by means of thermal or centrifugal field-flow fractionation. The method comprises the following steps:
(i) injection of a sample into the separation channel using a solvent,
(ii) equilibration of the sample in the separation channel, and
(ii) elution of the sample with the solvent from the separation channel under the influence of a separation field and detection of the fractionated sample with one or more detector(s), wherein sample-free solvent is simultaneously removed from the separation channel via the second outlet of the separation channel and the second mass flow controller arranged downstream of said outlet.

Removing of sample-free solvent during elution in the described method via the second outlet of the separation channel leads to concentration of the sample in the remaining solvent, which is led out of the separation channel through the detector(s).

In the method for analyzing a sample by means of flow field-flow fractionation, sample-free solvent may also be removed during the injection in step (i) and focusing in step (ii) via the second outlet of the separation channel and the second mass flow controller arranged downstream of said outlet.

In connection with the present invention, the term "injection" means introducing the sample into the solvent by means of the sample injection system of the apparatuses of the invention and flushing the sample into the separation channel together with the solvent.

In connection with the present invention, the term "focusing" means enriching the sample at a certain place in the separation channel in the form of a narrow band. During focusing, solvent is pumped into the inlet and the first outlet of the separation channel of the apparatuses of the invention for flow field-flow fractionation or, in the case of a corresponding AF4 separation channel, through the inlet and the additional connection for the focus flow. The sample is focused in the region of the colliding solvent streams inside the separation channel, usually at the front end of the separation channel.

In connection with the present invention, the term "equilibration" means establishing of a state of equilibrium, in which the individual sample particles are present within the separation channel in separate layers with a specific layer thickness depending on the strength of the separation field and their respective diffusion coefficients. No solvent is pumped through the separation channel during equilibration. Instead, the solvent stream generated by the pump is led past the separation channel through the detector(s).

In connection with the present invention, the term "elution" means flushing the sample out of the separation channel in the direction of the detector(s) with the aid of the solvent, wherein flushing is carried out under the influence of a separation field, the strength of which may be varied during elution depending on the type and size of the sample to be analyzed. During this process, sample-containing solvent is led through the first outlet towards the detector(s) and at the same time sample-free solvent is removed via the second outlet of the separation channel. This leads to concentration of the sample in the solvent, which is led through the first outlet for sample-containing solvent and through the detector(s).

The nature of the separation field applied during elution and detection is derived from the respective field-flow fractionation technique used. According to the invention this may be flow field-flow fractionation including symmetrical flow field-flow fractionation, asymmetrical flow field-flow fractionation (AF4) and hollow-fiber flow field-flow fractionation, sedimentation field-flow fractionation such as centrifugal field-flow fractionation or thermal field-flow fractionation.

In connection with the present invention, the term "detection" means detecting the sample by means of the detector(s) used and generating a corresponding measuring signal by the sample when this is guided through the detector(s) with the aid of the solvent.

In connection with the present invention, the term "analysis" means fractionating and detecting a sample by means of the apparatuses of the invention for field-flow fractionation.

In connection with the present invention, the term "sample" means any kind of analyte that may be fractionated and detected by means of the apparatuses of the invention. These can be substances of a molecular weight of 500 Da to 16 MDa or a size of 2 nm to 5 µm which are present in the solvent used either in a dissolved or a suspended form.

In particular, the term "sample" also includes mixtures wherein the molecular weight and/or the size of the individual components may be the same or different.

Samples for fractionation and detection by means of the apparatuses of the invention are, for example, proteins from the field of the pharmaceutical industry and research, nanoparticles and carbon nanotubes as well as natural and synthetic polymers, especially silicates, pigments, colloids, peptides, virus cells, liposomes, antibodies, polysaccharides and other macromolecules.

WAYS FOR CARRYING OUT THE INVENTION

In the following, preferred embodiments of the apparatuses of the invention will be explained with reference to the attached drawings and the reference signs used therein.

Figure 1:
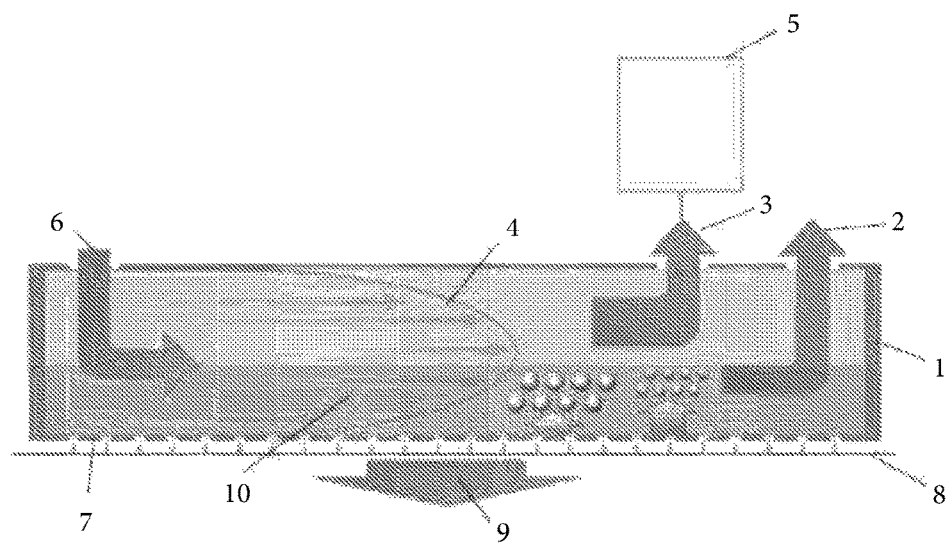
FIG. 1 shows the schematic set-up of an AF4 separation channel that, in addition to the first outlet for sample-containing solvent, comprises a second outlet for sample-free solvent, which is arranged in a region of the separation channel from which sample-free solvent may be removed during elution and which, according to the invention, is connected with a mass flow controller arranged downstream.

FIG. 1 shows the schematic set-up of an AF4 separation channel that, in addition to the first outlet for sample-containing solvent, comprises a second outlet for sample-free solvent, which according to the invention is connected with a mass flow controller arranged downstream as a flow volume control device.

The separation channel (1) has a first outlet for sample-containing solvent (2) and a second outlet for sample-free solvent (3). The separation channel (1) further comprises an inlet (6) and a semi-permeable size exclusion membrane (7) lying on the accumulation wall (8).

The cross-flow (9) applied during elution brings about enrichment of the sample in the region of the accumulation wall (8). The sample-containing solvent (10) present in this region is flushed out of the separation channel (1) through the first outlet (2) in the direction of the detector(s). The second outlet (3) is arranged in a region of the separation channel (1), from which sample-free solvent (4) may be removed during elution.

The mass flow controller (5) is arranged downstream of the second outlet (3).

Figure 2:
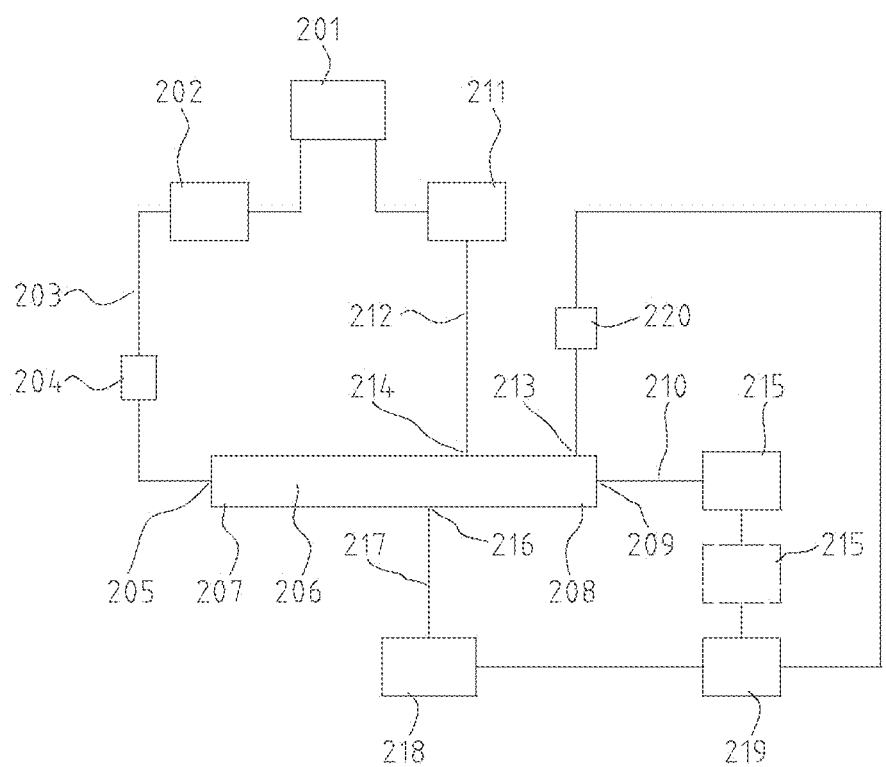
FIG. 2 shows the schematic set-up of an apparatus of the invention for flow field-flow fractionation with two pumps.

FIG. 2 shows the schematic set-up of an apparatus of the invention for flow field-flow fractionation with two pumps.

The apparatus comprises a reservoir (201), a first pump (202), a second pump (211), a sample injection system (204), a separation channel (206) with an inlet (205) at a first end (207), a first outlet (209) for sample-containing solvent at a second end (208), a connection (216) for the cross-flow and a second outlet (213) for sample-free solvent, which is arranged upstream of the first outlet (209), and an additional connection (214) for the focus flow, which is arranged between the inlet (205) and the second outlet (213), a mass flow controller (220) arranged downstream of the second outlet (213) and comprising a measuring unit, a regulating valve and a control line, one or more detector(s) (215), a cross-flow control device (218) and a waste container (219).

By means of the first pump (202) the solvent stream of the first flow path (203) is generated and leads via the sample injection system (204) to the inlet (205) at the first end (207) of the separation channel (206). The separation channel is preferably an AF4 separation channel.

By means of the second pump (211) the solvent stream of the second flow path (212) is generated and leads to the additional connection (214) for the focus flow.

A third flow path (210) leads from the first outlet for sample-containing solvent (209) at the second end (208) of the separation channel (206) to the detector(s) (215).

A fourth flow path (217) connects the connection (216) for the cross-flow with the cross-flow control device (218). The cross-flow control device (218) controls/regulates the flow through the size exclusion membrane of the separation channel (206), i.e. the separation field/the cross-flow, and thus influences the separation performance of the illustrated flow field-flow fractionation apparatus.

Separation of a sample by means of the apparatus of the invention shown in FIG. 2 consists of three steps.

In the first step, the sample is introduced from the sample injection system (204) and conveyed via the first flow path (203) into the separation channel (206).

In the second step, the sample is focused at the front end of the separation channel (206). During this step, solvent is conveyed by the first pump (202) at a flow rate in the range from 0.01 ml/min to 0.5 ml/min along the first flow path (203) into the separation channel (206). At the same time, the second pump (211) conveys a correspondingly larger solvent stream through the second flow path (212) and through the additional connection (214) for the focus flow into the separation channel (206). This results in division of the solvent stream so that one portion of the solvent flows through the first outlet (209) out of the separation channel (206) in the direction of the third flow path (210) and another portion of the solvent flows through the separation channel (206) in the opposite direction. In this way the sample is focused in the region of the colliding solvent streams at the front end of the separation channel (206). Meanwhile, the cross-flow control device (218) is active and is controlled in such a manner that the solvent stream through the cross-flow control device (218) is somewhat smaller than the solvent stream out of the two pumps (202) and (211) into the system. Thus, a controlled solvent stream in the direction of the detector(s) (215) results in the third flow path (210). At the same time, a back-pressure necessary for operation of the cross-flow control device (218) is generated in the separation channel (206).

The regulating valve of the mass flow controller (220) downstream of the second outlet (213) of the separation channel (206) can be open or closed in the first and in the second step. If the control valve is closed, no solvent is removed via the second outlet (213) during injection and focusing of the sample.

In the third step, the sample injected into the separation channel (206) via the sample injection system (204) is eluted from the separation channel (206) after focusing. For this purpose, the solvent stream through the second flow path (212) must be stopped. At the same time, the solvent stream through the first flow path (203) must be increased by the amount of the previous solvent stream through the second flow path (212) so as to ensure a constant solvent stream in the third flow path (210) and thus through the detector(s) (215). During elution, the entire solvent stream conveyed by the first pump (202) is led into the separation channel (206) via the first flow path (203). At the same time, a separation field (cross-flow) is applied in the separation channel (206).

The strength of the separation field is controlled by the cross-flow control device (218). The separation field, i.e. the cross-flow, results in a movement of the sample towards the accumulation wall of the separation channel (206) and to enrichment of the sample in the region of the accumulation wall (cf. FIG. 1). The other regions of the separation channel, in particular the regions of the separation channel opposite the accumulation wall, do not therefore contain any sample and hence are sample free. The sample-free solvent is removed through the second outlet (213) of the separation channel (206) via the mass flow controller (220). The sample-containing solvent is led through the first outlet (209) into the third flow path (210) and through the detector(s) (215).

During elution, the solvent stream conveyed by the pump (202) is controlled depending on the strength of the cross-flow in such a manner that the solvent stream through the third flow path (210) and hence through the detector(s) (215) remains constant.

The flows described for the individual steps are time-regulated by suitable software.

Figure 3:
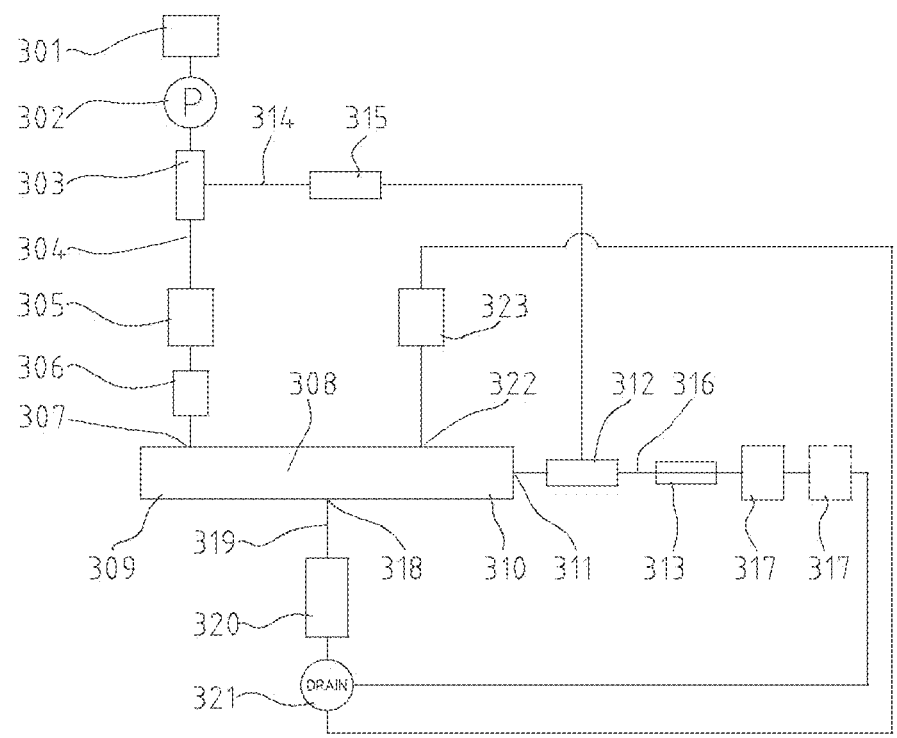
FIG. 3 shows the schematic set-up of an apparatus of the invention for flow field-flow fractionation with one pump.

FIG. 3 shows the schematic design of an apparatus of the invention for flow field-flow fractionation with one pump.

The apparatus comprises a reservoir (301), a pump (302), a first flow volume splitting device (303) a first mass flow controller (305) arranged downstream of the flow volume splitting device (303) and comprising a measuring unit, a regulating valve and a control line, a sample injection system (306), a separation channel (308) with an inlet (307) at a first end (309), a first outlet (311) for sample-containing solvent at a second end (310), a connection (318) for the cross-flow and a second outlet (322) for sample-free solvent, which is arranged between the inlet (307) and the first outlet (311), a second mass flow controller (323) arranged downstream of the second outlet (322) and comprising a measuring unit, a regulating valve and a control line, a second flow volume splitting device (312), a first back-pressure element (313), a second back-pressure element (315), one or more detector(s) (317), a cross-flow control device (320) and a waste container (321).

Having passed the reservoir (301) and the pump (302), the solvent stream generated by the pump (302) is divided by means of the flow volume splitting device (303), such as a T-connector, for example, into a first flow path (304) and a second flow path (314). The first flow path (304) initially leads to the first mass flow controller (305) with measuring unit, regulating valve and control line. The regulating valve is controlled via the control line in accordance with a target/actual value comparison of the data obtained with the measuring unit. The first flow path then leads via the sample injection system (306) to the inlet (307) at the first end (309) of the separation channel (308). The separation channel is preferably an AF4 separation channel.

The second flow path (314) leads to a second flow volume splitting device (312), such as a T-connector, for example. This divides the solvent stream between the first outlet (311) for sample-containing solvent at the second end (310) of the separation channel (308) and a third flow path (316), which leads via the first back-pressure element (313) to the detector(s) (317).

The first back-pressure element (313) is preferably a back-pressure capillary which, depending on the flow rate applied, generates a suitable back-pressure on the system. The back-pressure is necessary to apply pressure to the separation channel (308) and thus to the cross-flow control device (320) which is connected to the separation channel (308) via a fourth flow path (319) and the connection (318)

for the cross-flow so that the cross-flow control device can work. The cross-flow control device (320) controls/regulates the flow through the size exclusion membrane of the separation channel (308), i.e. the separation field/the cross-flow, and thus influences the separation performance of the illustrated flow field-flow fractionation apparatus.

The second back-pressure element (315) is integrated into the second flow path (314). The second back-pressure element (315) is preferably a back-pressure regulator which comprises a stamp which is pressed into a sealing seat by a spring against the direction of the flow.

Separation of a sample by means of the apparatus of the invention shown in FIG. 3 consists of three steps.

In the first step, the sample is introduced from the sample injection system (306) and conveyed via the first flow path (304) into the separation channel (308).

In the second step, the sample is focused at the front end of the separation channel (308). During this step, solvent is conveyed at a flow rate in the range from 0.01 ml/min to 0.5 ml/min along the first flow path (304) into the separation channel (308). At the same time, a further, correspondingly larger solvent stream is conveyed through the second flow path (314) via the second back-pressure element (315). Owing to the back-pressure generated by means of the back-pressure element (313), one portion of the solvent flows via the second flow volume splitting device (312) in the opposite direction through the first outlet (311) into the separation channel (308), while another portion of the solvent flows in the direction of the third flow path (316). In this way the sample is focused in the region of the colliding solvent streams at the front end of the separation channel (308). Meanwhile, the cross-flow control device (320) is active and is controlled in such a manner that the solvent stream through the cross-flow control device (320) is somewhat smaller than the solvent stream out of the pump (302) into the system. Thus, a controlled solvent stream in the direction of the detector(s) (317) results in the third flow path (316). By means of the first back-pressure element (313), the back-pressure described above which is necessary for the operation of the cross-flow control device (320) is generated in the separation channel (308).

The regulating valve of the second mass flow controller (323) downstream of the second outlet (322) of the separation channel (308) can be open or closed in the first and in the second step. If the control valve is closed, no solvent is removed via the second outlet (322) during injection and focusing of the sample.

In the third step, the sample injected into the separation channel (308) via the sample injection system (306) is eluted from the separation channel (308) after focusing. For this purpose, the solvent stream through the second flow path (314) must be stopped. At the same time, the solvent stream through the first flow path (304) must be increased by the amount of the previous solvent stream through the second flow path (314) so as to ensure a constant solvent stream in the third flow path (316) and thus through the detector(s) (317). During elution, the entire solvent stream conveyed by the pump (302) is led into the separation channel (308) via the first flow path (304). At the same time, a separation field (cross-flow) is applied in the separation channel (308). The strength of the separation field is controlled by the cross-flow control device (320). The separation field, i.e. the cross-flow, results in a movement of the sample towards the accumulation wall of the separation channel (308) and to enrichment of the sample in the region of the accumulation wall (cf. FIG. 1). The other regions of the separation channel, in particular the regions of the separation channel opposite the accumulation wall, do not therefore contain any sample and hence are sample free. The sample-free solvent is removed through the second outlet (322) of the separation channel (308) via the second mass flow controller (323). The sample-containing solvent is led through the first outlet (311) into the third flow path (316) and through the detector (s) (317).

During elution, the solvent stream conveyed by the pump (302) is controlled depending on the strength of the cross-flow in such a manner that the solvent stream through the third flow path (316) and hence through the detector(s) (317) remains constant.

The flows described for the individual steps are time-regulated by suitable software.

While the sample is being injected and focused, the flow rate in the first flow path (304) with the first mass flow controller (305) is 0.01 ml/min to 0.5 ml/min. After the sample has been injected and focused, i.e. during elution, the regulating valve of the first mass flow controller (305) in the first flow path (304) is no longer needed for controlling the volumetric flows and is therefore fully opened.

The second back-pressure element (315) in the second flow path (314) is set so that it is opened when the regulating valve of the first mass flow controller (305) in the first flow path (304) is active and at the same time the back-pressure through the entire first flow path (304) is higher than the back-pressure through the second flow path (314). Consequently, the pressure at the inlet of the first mass flow controller (305) is higher than the pressure in the separation channel (308), which is approximately equal to the pressure at the outlet of the regulating valve. As a result, the pressure differential at the first mass flow controller (305) is approximately equal to the pressure differential at the second back-pressure element (315).

If, after the sample has been introduced and focused, the regulating valve of the first mass flow controller (305) is fully opened, the back pressure through the first flow path (304) decreases and falls below the threshold value from which the second back-pressure element (315) opens the second flow path (314). Thus the stamp in the second back-pressure element (315) closes and blocks the second flow path (314). As a result, the entire solvent stream conveyed by the pump (302) reaches the separation channel (308) via the first flow path (304). Regulation of the flow through the first mass flow controller (305) is no longer necessary, since the solvent reaches the system only through the first flow path (304) and the flow rate is determined by the pump (302).

Figure 4:
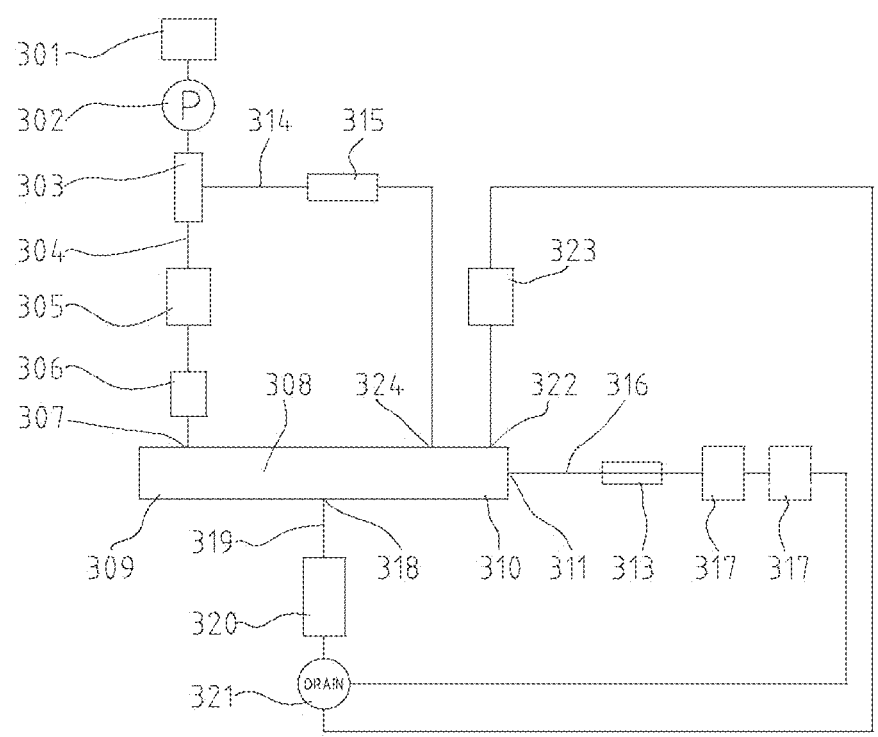
FIG. 4 shows the schematic set-up of an apparatus of the invention for flow field-flow fractionation with one pump and a separation channel with an additional connection for the focus flow.

FIG. 4 shows the schematic set-up of an apparatus of the invention for flow field-flow fractionation with one pump and a separation channel with an additional connection for the focus flow.

The apparatus comprises a reservoir (301), a pump (302), a first flow volume splitting device (303), a first mass flow controller (305) comprising a measuring unit, a regulating valve and a control line and arranged downstream of the flow volume splitting device (303), a sample injection system (306), a separation channel (308) with an inlet (307) at a first end (309), a first outlet (311) for sample-containing solvent at a second end (310), a connection (318) for the cross-flow and a second outlet (322) for sample-free solvent, which is arranged upstream of the first outlet (311), and an additional connection (324) for the focus flow, which is arranged between the inlet (307) and the second outlet (322), a second mass flow controller (323) arranged downstream of the second outlet (322) and comprising a measuring unit, a regulating valve and a control line, a first back-pressure element (313), a second back-pressure element (315), one or more detector(s) (317), a cross-flow control device (320) and a waste container (321).

Having passed the reservoir (301) and the pump (302), the solvent stream generated by the pump (302) is divided by means of the flow volume splitting device (303), such as a T-connector, for example, into a first flow path (304) and a second flow path (314). The first flow path (304) initially leads to the first mass flow controller (305) with measuring unit, regulating valve and control line. The regulating valve is controlled via the control line in accordance with a target/actual value comparison of the data obtained with the measuring unit. The first flow path then leads via the sample injection system (306) to the inlet (307) at the first end (309) of the separation channel (308). The separation channel is preferably an AF4 separation channel.

The second flow path (314) leads to the additional connection (324) for the focus flow.

A third flow path (316) leads from the first outlet for sample-containing solvent (311) at the second end (310) of the separation channel (308) via the first back-pressure element (313) to the detector(s) (317).

The second back-pressure element (315) is integrated into the second flow path (314). The second back-pressure element (315) is preferably a back-pressure regulator which comprises a stamp which is pressed into a sealing seat by a spring against the direction of the flow.

In terms of the function and the effect of the first back-pressure element (313) and the second back-pressure element (315) integrated in the second flow path (314), the apparatus shown in FIG. 4 corresponds to that shown in FIG. 3. The corresponding explanations regarding FIG. 3 thus also apply to FIG. 4.

Separation of a sample by means of the apparatus of the invention shown in FIG. 4 consists of three steps.

In the first step, the sample is introduced from the sample injection system (306) and conveyed via the first flow path (304) into the separation channel (308).

In the second step, the sample is focused at the front end of the separation channel (308). During this step, solvent is conveyed at a flow rate in the range from 0.01 ml/min to 0.5 ml/min along the first flow path (304) into the separation channel (308). At the same time, a further, correspondingly larger solvent stream is conveyed through the second flow path (314) via the second back-pressure element (315) and the solvent flows through the additional connection (324) for the focus flow into the separation channel (308). Due to the back-pressure generated with the aid of the back-pressure element (313), the solvent stream is divided in such a manner that one portion of the solvent flows through the outlet (311) from the separation channel (308) in the direction of the third flow path (316) and another portion of the solvent flows through the separation channel (308) in the opposite direction. In this way the sample is focused in the region of the colliding solvent streams at the front end of the separation channel (308). Meanwhile, the cross-flow control device (320) is active and is controlled in such a manner that the solvent stream through the cross-flow control device (320) is somewhat smaller than the solvent stream out of the pump (302) into the system. Thus, a controlled solvent stream in the direction of the detector(s) (317) results in the third flow path (316). By means of the first back-pressure element (313), the back-pressure described above which is necessary for the operation of the cross-flow control device (320) is generated in the separation channel (308).

The regulating valve of the second mass flow controller (323) downstream of the second outlet (322) of the separation channel (308) can be open or closed in the first and in the second step. If the control valve is closed, no solvent is removed via the second outlet (322) during injection and focusing of the sample.

In the third step, the sample injected into the separation channel (308) via the sample injection system (306) is eluted from the separation channel (308) after focusing. For this purpose, the solvent stream through the second flow path (314) must be stopped. At the same time, the solvent stream through the first flow path (304) must be increased by the amount of the previous solvent stream through the second flow path (314) so as to ensure a constant solvent stream in the third flow path (316) and thus through the detector(s) (317).

During elution, the entire solvent stream conveyed by the pump (302) is led into the separation channel (308) via the first flow path (304). At the same time, a separation field (cross-flow) is applied in the separation channel (308). The strength of the separation field is controlled by the cross-flow control device (320). The separation field, i.e. the cross-flow, results in a movement of the sample towards the accumulation wall of the separation channel (308) and to enrichment of the sample in the region of the accumulation wall (cf. FIG. 1). The other regions of the separation channel, in particular the regions of the separation channel opposite the accumulation wall, do not therefore contain any sample and hence are sample free. The sample-free solvent is removed through the second outlet (322) of the separation channel (308) via the second mass flow controller (323). The sample-containing solvent is led through the first outlet (311) into the third flow path (316) and through the detector(s) (317).

During elution, the solvent stream conveyed by the pump (302) is controlled depending on the strength of the cross-flow in such a manner that the solvent stream through the third flow path (316) and hence through the detector(s) (317) remains constant.

The flows described for the individual steps are time-regulated by suitable software.

In terms of the function and the effect of the first mass flow controller (305) and its interaction with the second back-pressure element (315), the apparatus shown in FIG. 4 corresponds to that shown in FIG. 3. The corresponding explanations regarding FIG. 3 thus also apply to FIG. 4.

Figure 5:
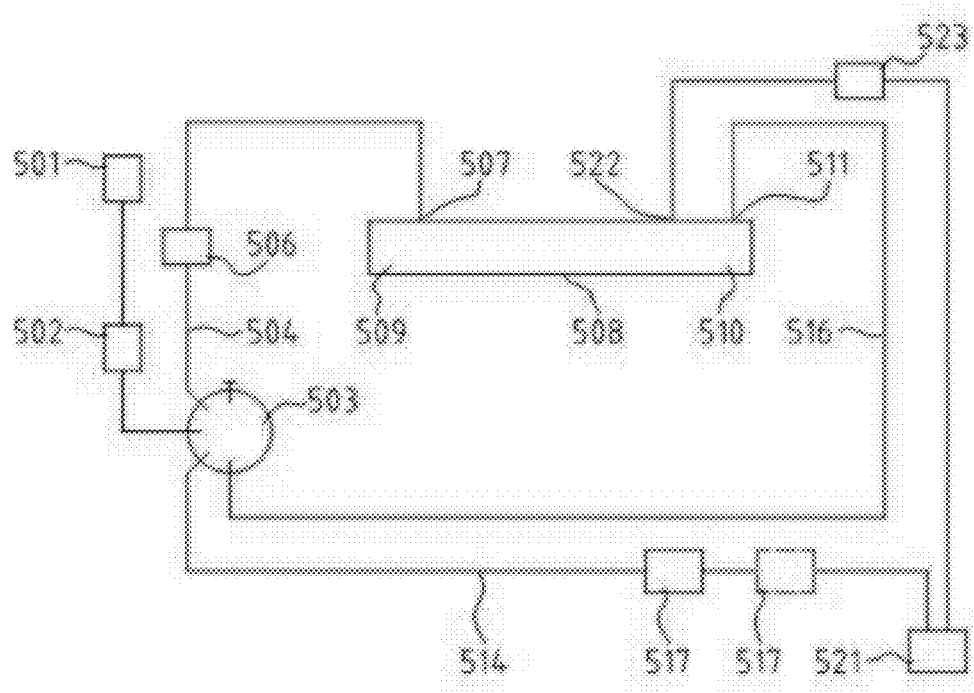
FIG. 5 shows the schematic set-up of an apparatus of the invention for centrifugal and thermal field-flow fractionation.

FIG. 5 shows the schematic set-up of an apparatus of the invention for centrifugal and thermal field-flow fractionation.

The apparatus comprises a reservoir (501), a pump (502), a flow volume splitting device (503), a sample injection system (506) arranged downstream of the flow volume splitting device (503), a separation channel (508) with an inlet (507) at a first end (509), a first outlet (511) for sample-containing solvent at a second end (510), a second outlet (522) for sample-free solvent, which is arranged between the inlet (507) and the first outlet (511), a mass flow controller (523) arranged downstream of the second outlet (522) and comprising a measuring unit, a regulating valve and a control line, one or more detector(s) (517) and a waste container (521).

Having passed the reservoir (501) and the pump (502), the solvent stream generated by the pump (502) is divided by means of the flow volume splitting device (503), such as a switching valve, for example, into a first flow path (504), a second flow path (514) and a third flow path (516). The first flow path (504) leads via the sample injection system (506) to the inlet (507) at the first end (509) of the separation channel (508). The separation channel (508) is optionally a separation channel for centrifugal or thermal field-flow fractionation.

The second flow path (514) connects the flow volume splitting device (503) with the detector(s) (517).

The third flow path (516) connects the flow volume splitting device (503) with the first outlet (511) of the separation channel (508).

Separation of a sample by means of the apparatus of the invention shown in FIG. 5 consists of three steps.

In the first step, the sample is introduced from the sample injection system (506) and conveyed via the first flow path (504) into the separation channel (508).

In the second step, the sample is equilibrated in the separation channel (508). During this step, solvent is conveyed at a flow rate in the range from 0.01 ml/min to 4 ml/min via the flow volume splitting device (503) along the second flow path (514) past the separation channel (508) to the detector(s) (517) and to the waste container (521).

During this step, the regulating valve of the second mass flow controller (523) downstream of the second outlet (522) of the separation channel (508) is closed so that no solvent is removed via the second outlet (522) during equilibration of the sample.

In the third step, the solvent stream is led from the pump (502) via the flow volume splitting device (503), the first flow path (504) and the inlet (507) into the separation channel (508) and the sample that has previously been introduced in the first step and equilibrated in the second step is eluted out of the separation channel (508). At the same time, a separation field is applied in the separation channel (508). The separation field results in a movement of the sample towards the accumulation wall of the separation channel (508) and to enrichment of the sample in the region of the accumulation wall (cf. FIG. 1). The other regions of the separation channel, in particular the regions of the separation channel opposite the accumulation wall, do not therefore contain any sample and hence are sample free. The sample-free solvent is removed through the second outlet (522) of the separation channel (508) via the mass flow controller (523). The sample-containing solvent is led through the first outlet (511) via the third flow path (516) and the flow volume splitting device (503) into the second flow path (514) and through the detector(s) (517).

The separation field applied during elution in the third step can be a thermal field within the separation channel (508) or a centrifugal force that is generated by rotating the separation channel (508).

The flows described for the individual steps are time-regulated by suitable software.

EXAMPLE

In a comparative test, the baseline signal of the RI detector of an apparatus of the invention for flow field-flow fractionation was compared with the baseline signal of the RI detector of a flow field-flow fractionation apparatus known from the prior art.

The measurements were performed with a flow field-flow fractionation system made by Postnova Analytics GmbH Landsberg, Germany. The following settings were used for this.

Figure 6:
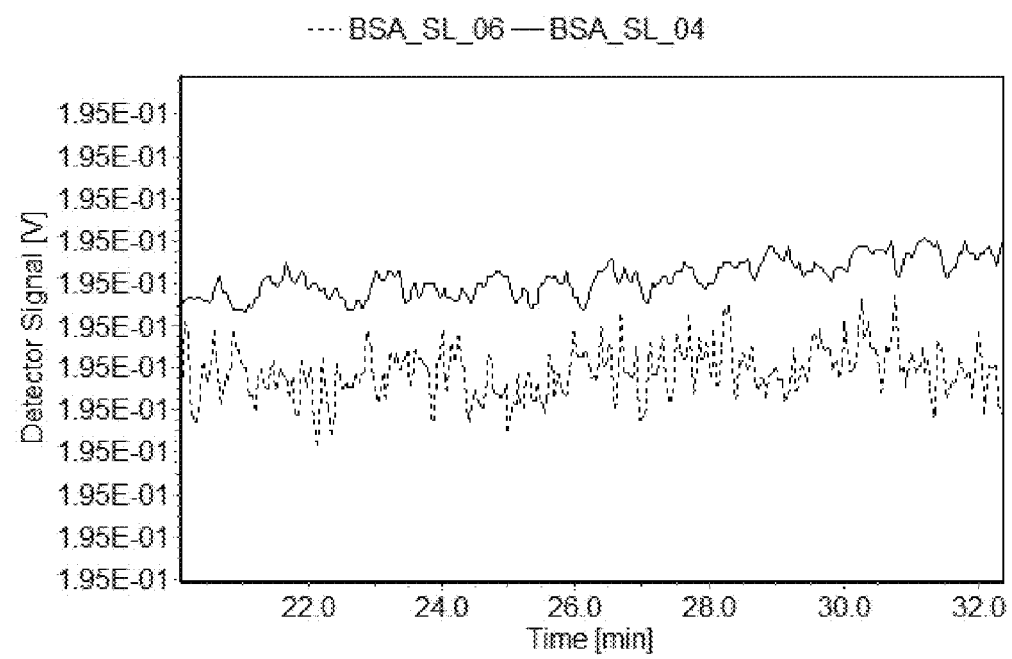
FIG. 6 shows a comparison between the baseline signal of a refractive index (RI) detector that was obtained with an apparatus of the invention with a mass flow controller as flow volume control device for the sample-free solvent removed from the separation channel and the baseline signal of an RI detector that was obtained with an apparatus known from the prior art with a syringe pump as flow volume control device for the sample-free solvent removed from the separation channel.

Separation channel: AF4 separation channel with a cut-off of 10 kDa, comprising a second outlet for sample-free solvent and a syringe pump or a mass flow controller for removing the Slot Outlet flow, said syringe pump or mass flow controller being arranged downstream of said second outlet and connected to it via a capillary Sample Bovine Serum Albumin (BSA), molecular weight approx. 66 kDa Cross-flow: 4 ml/min Flow rate through the detector: 0.3 ml/min Flow rate through the mass flow controller: 0.7 ml/min Detector: RI detection Solvent: 0.2% NaCl in water The results are shown in FIG. 6. They show a clear improvement in the signal-to-noise ratio for the apparatus of the invention. Compared with the conventional apparatus (dotted line, BSA_SL_06), a reduction in the baseline noise by approximately half could be achieved with the apparatus of the invention (solid line, BSA_SL_04).

LIST OF REFERENCE SIGNS 1 separation channel
2 first outlet for sample-containing solvent
3 second outlet for sample-free solvent
4 sample-free solvent
5 mass flow controller
6 inlet
7 semi-permeable size exclusion membrane
8 accumulation wall
9 cross-flow
10 sample-containing solvent
201 reservoir
202 first pump
203 first flow path
204 sample injection system
205 inlet
206 separation channel
207 first end
208 second end
209 first outlet
210 third flow path
211 second pump
212 second flow path
213 second outlet
214 additional connection for the focus flow
215 detector(s)
216 connection for the cross-flow
217 fourth flow path
218 cross-flow control device
219 waste container
220 mass flow controller
301 reservoir
302 pump
303 first flow volume splitting device
304 first flow path
305 first mass flow controller
306 sample injection system
307 inlet
308 separation channel
309 first end
310 second end
311 first outlet
312 second flow volume splitting device
313 first back-pressure element
314 second flow path
315 second back-pressure element
316 third flow path
317 detector(s)
318 connection for the cross-flow
319 fourth flow path 320 cross-flow control device
321 waste container
322 second outlet
323 second mass flow controller
324 additional connection for the focus flow
501 reservoir
502 pump
503 flow volume splitting device
504 first flow path
506 sample injection system
507 inlet
508 separation channel
509 first end
510 second end
511 first outlet
514 second flow path
516 third flow path
517 detector(s)
521 waste container
522 second outlet
523 mass flow controller

The invention claimed is:

1. Apparatus for field-flow fractionation, comprising a separation channel, which, in addition to a first outlet for sample-containing solvent, comprises a second outlet for sample-free solvent, wherein
the solvent is a liquid,
the second outlet is arranged in a region of the separation channel from which sample-free solvent can be removed during elution simultaneously to removal of sample-containing solvent from the first outlet and wherein the second outlet is arranged upstream of the first outlet and opposite an accumulation wall of the separation channel, and
a flow volume control device is arranged downstream of the second outlet,
characterized in that the flow volume control device is a mass flow controller, and wherein the apparatus further comprises;
a pump, a first flow volume splitting device, a first mass flow controller arranged downstream of the flow volume splitting device, a sample injection system, the separation channel with an inlet at a first end, the first outlet for sample-containing solvent at a second end, a connection for a cross-flow and the second outlet for sample-free solvent, which is arranged between the inlet and the first outlet, a second mass flow controller arranged downstream of the second outlet, a second flow volume splitting device, a first back-pressure element, a second back-pressure element, one or more detector(s) and a cross-flow control device, wherein
a solvent stream generated by the pump is divided by means of the first flow volume splitting device into a first flow path and a second flow path,
the first flow path leads via the first mass flow controller and the sample injection system to the inlet at the first end of the separation channel,
the second flow path leads via the second back-pressure element to the second flow volume splitting device, which divides the solvent stream between the first outlet for sample-containing solvent at the second end of the separation channel and a third flow path, which leads via the first back-pressure element to the detector(s), and
the cross-flow control device is connected with the separation channel via a fourth flow path and the connection for the cross-flow.

2. Apparatus according to claim 1, wherein the separation channel is a separation channel for symmetrical flow field-flow fractionation, or asymmetrical flow field-flow fractionation.

3. Apparatus according to claim 1, wherein the mass flow controller comprises a measuring unit, a control valve and a control line.

4. Apparatus according to claim 1, wherein the separation channel is a separation channel for asymmetrical flow field-flow fractionation.

5. Apparatus according to claim 4, wherein the detector(s) is/are a UV detector, a refractive index detector and/or a (multi-angle) light scattering detector.

6. Apparatus according to claim 1, wherein the detector(s) is/are a UV detector, a refractive index detector and/or a (multi-angle) light scattering detector.

7. Apparatus according to claim 1, wherein the mass flow controller arranged downstream of the second outlet of the separation channel is directly connected with the second outlet of the separation channel.

8. Apparatus according to claim 1, wherein a shut-off valve or switching valve is arranged between the second outlet of the separation channel and the mass flow controller arranged downstream of said outlet.

9. Apparatus according to claim 8, wherein the shut-off or switching valve is directly connected with the second outlet of the separation channel.

10. A method for analyzing a sample by means of field-flow fractionation using the apparatus according to claim 1 and comprising the following steps:
   (i) injection of a sample into the separation channel using a liquid solvent, and
   (ii) elution of sample containing solvent and sample-free solvent simultaneously from the separation channel under the influence of a separation field and detection of the fractionated sample with one or more detector(s), wherein
      (a) the sample-containing solvent is removed from the separation channel via the first outlet; and
      (b) sample-free solvent is removed from the separation channel via the second outlet of the separation channel and the mass flow controller arranged downstream of said second outlet.

11. A method for analyzing a sample by means of flow field-flow fractionation using the apparatus according to claim 1 and comprising the following steps:
   (i) injection of a sample into the separation channel using a solvent,
   (ii) focusing the sample with the aid of the solvent in the separation channel, and
   (iii) elution of the sample with the solvent from the separation channel under the influence of a separation field and detection of the fractionated sample with one or more detector(s), wherein sample-free solvent is simultaneously removed from the separation channel via the second outlet of the separation channel and the second mass flow controller arranged downstream of said outlet.

12. Method for analyzing a sample by means of flow field-flow fractionation according to claim 11, wherein sample-free solvent is removed from the separation channel also during the injection in step (i) and focusing in step (ii) via the second outlet of the separation channel and the second mass flow controller arranged downstream of said outlet.

* * * * *